(12) United States Patent
Deflorian et al.

(10) Patent No.: US 10,561,756 B2
(45) Date of Patent: *Feb. 18, 2020

(54) VOLATILE COMPOSITION DISPENSER WITH GUIDING MECHANISM

(71) Applicant: The Procter & Gamble Company, Cincinnati, OH (US)

(72) Inventors: Stefano Deflorian, Trento (IT); Walter Sordo, Trento (IT); Stefano Baldessari, Caldonazzo (IT); Ricard Tomas Vilarrasa, Trento (IT)

(73) Assignee: The Procter & Gamble Company, Cincinnati, OH (US)

( * ) Notice: Subject to any disclaimer, the term of this patent is extended or adjusted under 35 U.S.C. 154(b) by 142 days.

This patent is subject to a terminal disclaimer.

(21) Appl. No.: 15/582,849

(22) Filed: May 1, 2017

(65) Prior Publication Data
US 2017/0319734 A1     Nov. 9, 2017

Related U.S. Application Data

(60) Provisional application No. 62/330,872, filed on May 3, 2016.

(51) Int. Cl.
*A61L 9/12* (2006.01)
*B05B 12/00* (2018.01)

(52) U.S. Cl.
CPC ............ *A61L 9/12* (2013.01); *B05B 12/0022* (2018.08); *A61L 2209/13* (2013.01); *A61L 2209/131* (2013.01); *A61L 2209/133* (2013.01)

(58) Field of Classification Search
CPC .......... A61L 9/12–127; A61L 2209/13; A61L 2209/131; A61L 2209/133; A61L 2209/134; A01M 1/2044; A01M 1/2055

USPC ..................................................... 239/34–60
See application file for complete search history.

(56) References Cited

U.S. PATENT DOCUMENTS

| 4,526,320 A * | 7/1985 | von Philipp ........ A01M 1/2044 239/34 |
| 5,875,968 A * | 3/1999 | Miller .................... A61L 9/127 239/44 |
| 8,740,110 B2 | 6/2014 | Gruenbacher et al. |
| 8,931,711 B2 | 1/2015 | Gruenbacher et al. |
| 9,015,989 B1 * | 4/2015 | Zeamer ............... A01M 1/2005 239/37 |
| 9,439,993 B2 | 9/2016 | Gruenbacher et al. |

(Continued)

FOREIGN PATENT DOCUMENTS

| WO | WO 98/16262 A1 | 4/1998 |
| WO | WO 2006/061802 A1 | 6/2006 |

OTHER PUBLICATIONS

PCT Search Report PCT/US2017/030713; dated Jul. 26, 2017; 13 Pages.

(Continued)

*Primary Examiner* — Cody J Lieuwen
(74) *Attorney, Agent, or Firm* — Abbey A. Lopez (57) ABSTRACT

There is a volatile composition dispenser comprising a housing having a rear fram, a rupturable cartridge disposed within the housing and a button for rupturing the cartridge. The volatile composition dispenser further comprises a guiding mechanism for guiding movement of the button from a first position to a second position when the button is pressed.

15 Claims, 8 Drawing Sheets

FIG. 2

(56) References Cited

U.S. PATENT DOCUMENTS

| | | |
|---|---|---|
| 2010/0314461 A1 | 12/2010 | Gruenbacher et al. |
| 2011/0180621 A1 | 7/2011 | Gruenbacher et al. |
| 2012/0267279 A1* | 10/2012 | Lesniak .................. A61L 9/12 206/524.1 |
| 2012/0312706 A1* | 12/2012 | Isaac .................. B65D 81/32 206/222 |
| 2014/0103136 A1* | 4/2014 | Sidawi .................. A61L 9/127 239/44 |
| 2015/0060565 A1 | 3/2015 | Furner |
| 2016/0354505 A1 | 12/2016 | Gruenbacher et al. |
| 2017/0043047 A1 | 2/2017 | Beck et al. |

OTHER PUBLICATIONS

PCT Search Report PCT/US2017/030715; dated Jul. 26, 2017; 14 Pages.
PCT Search Report PCT/US2017/030716; dated Jul. 20, 2017; 13 Pages.
PCT Search Report PCT/US2017/030717; dated Sep. 11, 2017; 15 Pages.
U.S. Appl. No. 15/582,828, filed May 1, 2017, Hasenoehrl, et al.
U.S. Appl. No. 15/582,834, filed May 1, 2017, Hasenoehrl, et al.
U.S. Appl. No. 15/582,841, filed May 1, 2017, Hu, et al.
All Office Actions for U.S. Appl. No. 15/582,828.
All Office Actions for U.S. Appl. No. 15/582,834.
All Office Actions for U.S. Appl. No. 15/582,841.

* cited by examiner

VOLATILE COMPOSITION DISPENSER WITH GUIDING MECHANISM

FIELD OF THE INVENTION

The invention relates to the field of devices and systems for delivering a volatile composition and particularly relates to a volatile composition dispenser with a guiding mechanism, and a method of activating a volatile composition dispenser.

BACKGROUND OF THE INVENTION

Systems for delivering volatile materials to the atmosphere are well known in the art, and include for example, insect repellants, air fresheners, malodor removal agents. Such systems function by evaporating a volatile material through a medium such as a permeable membrane into a space to deliver a variety of benefits such as air freshening or malodor removal or a combination thereof. Typically, the volatile composition is stored in a sealed container that is opened or punctured to release the volatile composition to the air.

PCT Publication No. WO 98/16262 (hereinafter, "WO98/16262") describes a disposable air freshener dispenser device having a push-button actuator which can be manually operated to initiate the dispensing of air freshener composition into the atmosphere. The device of WO98/16262 has an air freshener medium within a container, and a push button actuator which can be manually operated to rupture a foil covering the container for initiating the dispensing of the air freshener into the atmosphere. A problem associated with such devices is that it is difficult for a user (such as a consumer) to determine whether the air freshener device is activated until the consumer smells the air freshener composition. As a result, if the consumer does not smell the air freshener composition, the consumer may consider that the device is not activated or is malfunctioning and this leads to reduced consumer satisfaction. Another problem of the prior art device is it is not easily detected by other users (such as retail store owners) whether such devices have been tampered with or inadvertently activated during handling or transportation to the retail stores. This may result in defective air freshener devices being displayed for sale which inevitably lead to consumer complaints when consumers purchase a defective air freshener device.

Therefore, there exists a need for an apparatus for delivering a volatile material that can be manually operated and provides a signal to users indicating activation of the apparatus at the same time.

SUMMARY OF THE INVENTION

In order to address the above-identified needs, the present invention provides a volatile composition dispenser comprising:
 a housing comprising a rear frame having a frame opening and a longitudinal axis extending centrally within said opening;
 a rupturable cartridge placed within said housing;
 an inner wall extending from the frame opening, wherein the inner wall has a proximal end at a periphery of the opening and a distal end;
 a push button disposed within the frame opening for rupturing the cartridge, wherein the button includes a button body and a top and is axially movable along and rotatable about the longitudinal axis at a rotation angle, β (degrees);
 a cam guide disposed on the inner wall or the button body, wherein the cam guide comprises a cam angle, α (degrees) relative to a cylindrical axis of the inner wall or the button body, wherein α>β; and
 a protrusion disposed on the other of the inner wall or the button body wherein the protrusion is engaged with the cam guide in response to the axial movement of the push button when pushed.

A technical effect of a protrusion engaged with a cam guide is that a push button is movable axially and rotatable simultaneously within the frame opening which results in a change in positions of the push button before and after activation. The change in the positions provides a visible signal to the user that the dispenser is activated.

BRIEF DESCRIPTION OF THE DRAWINGS

While the specification concludes with the claims particularly pointing out and distinctly claiming the invention, it is believed that the present invention will be better understood from the following description taken in conjunction with the accompanying drawings in which:

DETAILED DESCRIPTION OF THE INVENTION

The present invention relates to a volatile composition dispenser for the delivery of a volatile material to the atmosphere. The dispenser is suitable for purposes of providing fragrances, air fresheners, deodorizers, odor eliminators, malodor counteractants, insecticides, insect repellants, medicinal substances, disinfectants, sanitizers, mood enhancers, aromatherapy aids, or for any other purpose using a volatile material or a volatile composition that acts to condition, modify, or otherwise change the atmosphere or the environment. For the purposes of illustrating the present invention in detail, but without intending to limit the scope of the invention, the invention will be described in a volatile composition dispenser for delivering a liquid composition containing perfume raw materials.

Figure 1:
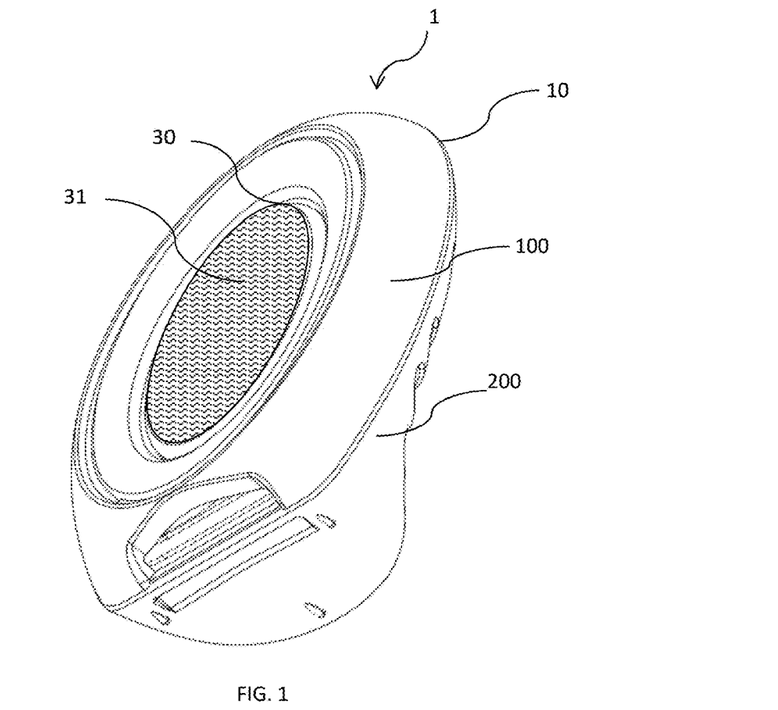
FIG. 1 is a front perspective view of a volatile composition dispenser according to an embodiment.
Figure 2:
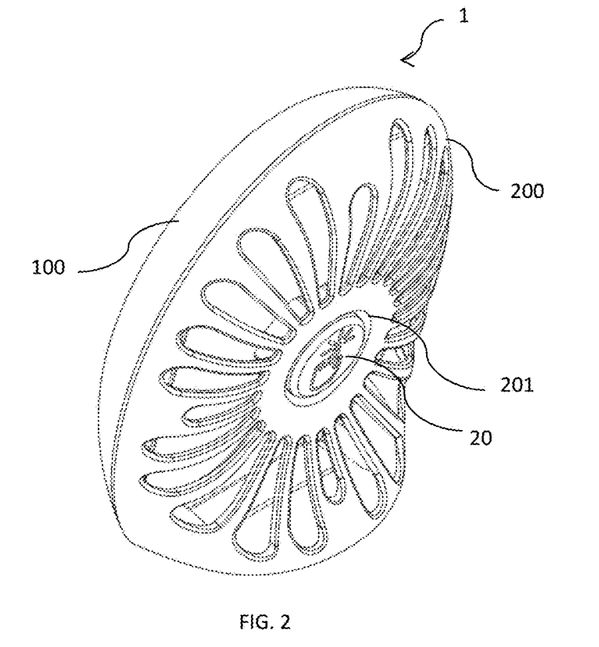
FIG. 2 is a rear perspective view of the volatile composition dispenser shown in FIG. 1.

FIG. 1 shows a front perspective view of a volatile composition dispenser 1 (hereinafter "dispenser") according to the present invention and FIG. 2 shows a rear perspective view of the dispenser 1. The dispenser 1 comprises a housing 10 having a front cover 100 and a rear frame 200, the front cover 100 and the rear frame 200 defining an interior space. The rear frame 200 is provided with a frame opening 201 (hereinafter "opening") located substantially in the centre of the rear frame 200. A push button 20 (hereinafter "button") is disposed within the opening 201 and is movable with respect to the rear frame 200 for enabling a user to activate the dispenser 1. A cartridge 30 containing a volatile composition 31 is located within the housing 10.

Figure 3:
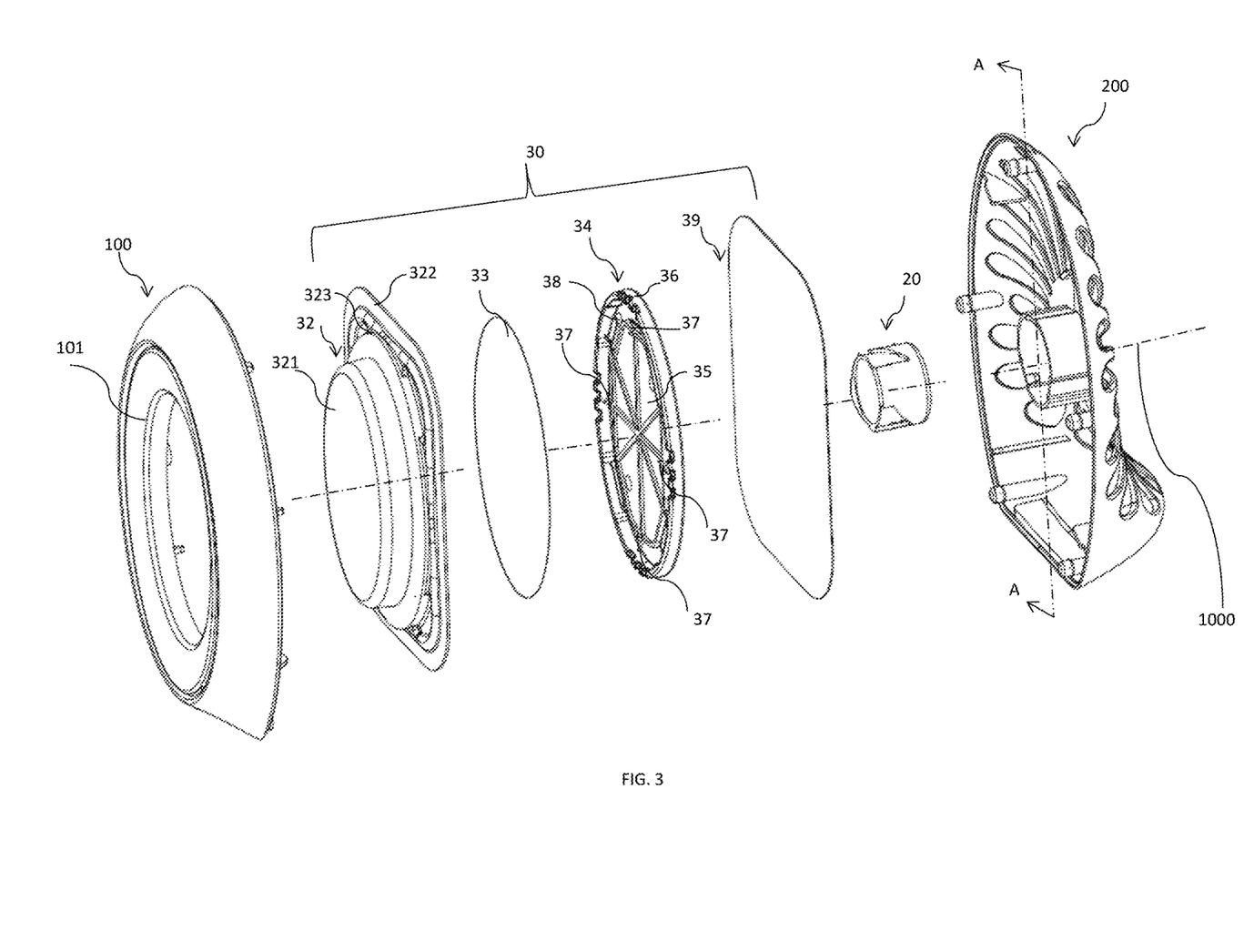
FIG. 3 is a side perspective exploded view of the volatile composition dispenser shown in FIG. 1.

FIG. 3 shows internal components of the dispenser 1. The front cover 100 comprises a window 101 configured for displaying the cartridge 30. The cartridge 30 comprises a container 32 having an orifice 321, within which the volatile composition 31 (as shown in FIG. 1) is stored. A rupturable substrate 33 is sealably attached to and covers the orifice 321 defining a reservoir to prevent the volatile composition 31 from being released until the dispenser 1 is activated. The rupturable substrate 33 may be ruptured to release the volatile composition 31 by actuating a rupture mechanism 34 positioned adjacent to the rupturable substrate 33. The rupture mechanism 34 comprises a movable member 35 movably attached to an outer frame 36 by a resilient member 38. The resilient member 38 may be formed of one or more springs 38. One or more rupture elements 37 are arranged within the rupture mechanism 34 to puncture holes in the rupturable substrate 33. The rupture element 37 may be a pin. The cartridge 30 may comprise a membrane 39 located on the exterior of the cartridge 30. The membrane 39 may be sealably attached to a flange 322 located at a periphery 323 of the container 32. The membrane 39 encloses the container 32, the volatile composition 31, the rupturable substrate 33, and the rupture mechanism 34. The membrane 39 may be configured to flex when a pressure or an actuation force is applied on the membrane 39.

To activate the dispenser 1, a user depresses the button 20 until it engages the rupture mechanism 34 (through deflection or flexing of the membrane 39), and the pins 37 on the rupture mechanism 34 pierce the rupturable substrate 33. Once the rupturable substrate 33 is pierced, the volatile composition 31 flows out of the container 32, wets the membrane 39 and is then delivered to the atmosphere surroundings through evaporation from the membrane 39.

The button 20 and the rear frame 200 may be configured to enable efficient and controlled rupturing of the rupturable substrate 33 in the cartridge 30 while additionally providing a tactile and intuitive user experience to the user for activating the dispenser 1.

Figure 4:
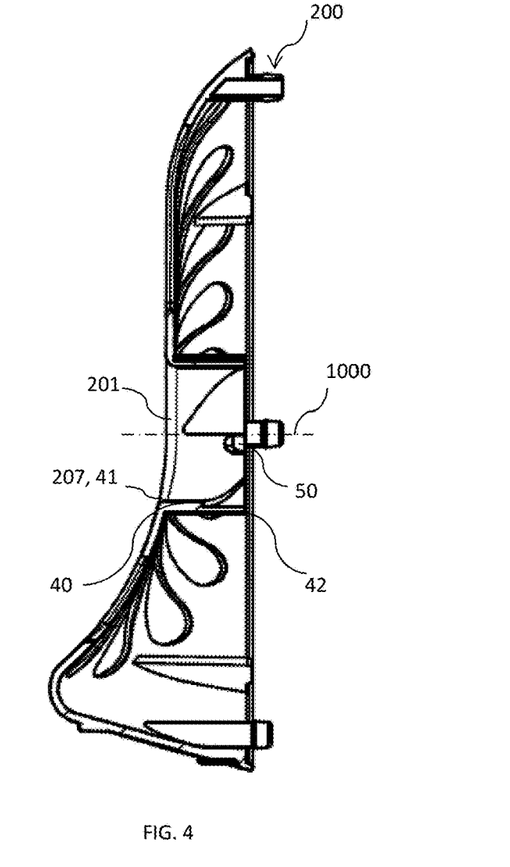
FIG. 4 is a side section view of a rear frame for a volatile composition dispenser according to an embodiment.

FIG. 4 shows a side section view A-A of the rear frame 200. An inner wall 40 is provided at a periphery 207 of the opening 201 and extends into the housing 10 from the interior of the rear frame 200. The inner wall 40 has a proximal end 41 flush with the periphery 207 of the opening 201, and a distal end 42 protruding into the housing 10. The inner wall 40 may be solid and tubular in shape. However, the inner wall 40 may take some other shape such as for example a square cross section or a rectangular cross section. The inner wall 40 may be substantially cylindrical and comprise a continuous wall, or a segmented wall such as for example, a lattice structure or multiple elongate struts connected to one another. The inner wall 40 may define an extension of the opening 201 into the housing 10 with a central longitudinal axis 1000 running through the centre of the opening 201 and along which the button 20 can be depressed. Alternatively, the inner wall 40 may protrude out of the housing 10 such that the inner wall 40 defines an extension of the opening 201 out of the housing 10. Accordingly, the distal end 42 may be flush with the periphery 207 of the opening 201 and the proximal end 41 may protrude out of the housing 10. At least one protrusion 50 may be located on the distal end 42 of the inner wall 40.

Figure 5:
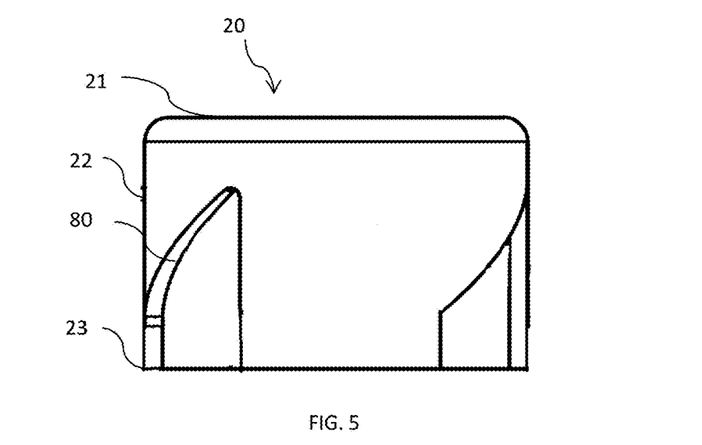
FIG. 5 is a front view of a button for a volatile composition dispenser according to an embodiment.

FIG. 5 is a front view of the button 20 configured to fit and to move within the opening 201 of the rear frame 200. The button 20 comprises a top 21 and a button body 22 extending from the top 21 into the housing 10. The top 21 is located in line with the periphery 207 of the opening 201 when the button 20 is in an "at rest" position (see for example FIG. 12A). Alternatively, the top 21 of the button 20 protrude out of the opening 201 when "at rest" (see for example. FIG. 13A). The button body 22 extends substantially in parallel to the inner wall 40. Therefore the button body 22 may also have a tubular shape. A cam guide 80 may be provided on the button body 22.

Figure 6A:
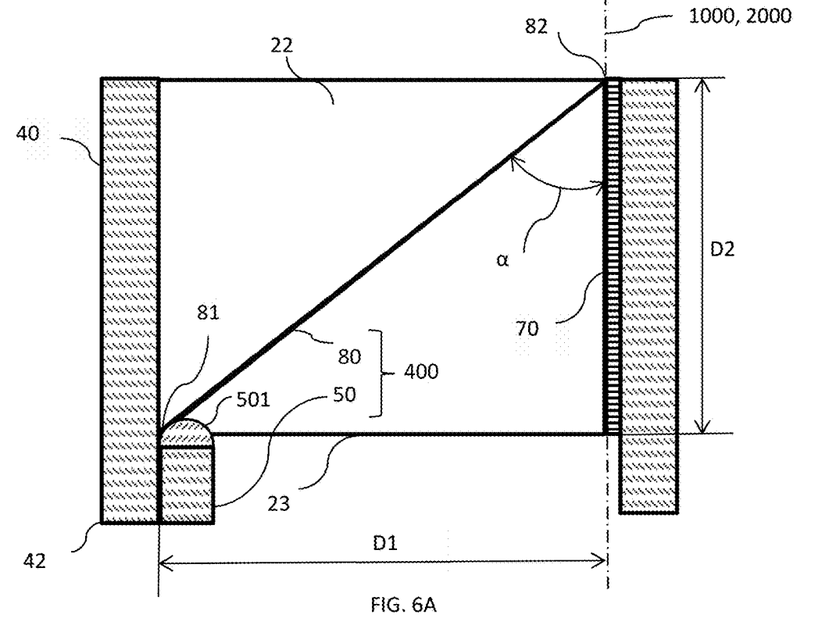
FIGS. 6A and 6B are schematic drawings which depict the movement of the button of FIG. 5 within the rear frame of FIG. 4.
Figure 6B:
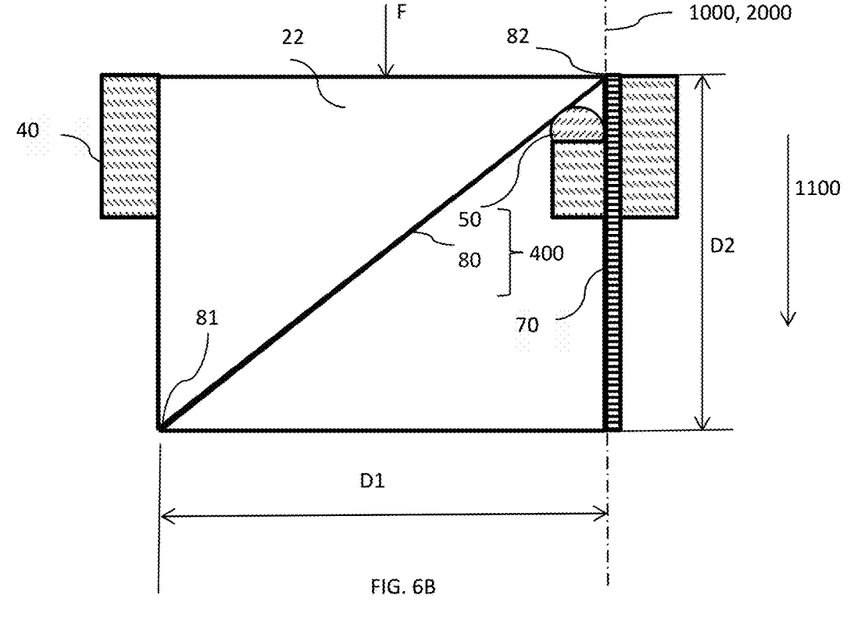

FIG. 6A is a cross-sectional view of the button 20 mounted within the rear frame 200 wherein the button 20 is in a "at rest" position. FIG. 6B is a cross-sectional view of the button 20 in a post-activation position. The button 20 is configured to move linearly in a plane parallel to the longitudinal axis 1000 and rotate about the longitudinal axis 1000 at the same time with respect to the rear frame 200 upon depression of the button 20.

Specifically, the dispenser 1 comprises a guiding mechanism 400 for guiding movement of the button 20 from the "at rest" position to the post-activation position by converting axial motion of the button 20 into rotation in response to a force applied on the top 21 of the button 20 by a user. Specifically, the guiding mechanism 400 is arranged between the button 20 and the inner wall 40 for guiding movement of the button 20. Specifically, the guiding mechanism 400 comprises at least one cam guide 80 located on one of the inner wall 300 and the button body 22 for converting an axial movement of the button 20 into rotation and at least one protrusion 50 located on the another one of the inner wall 40 and the button body 22. The protrusion 50 is engaged with the at least one cam guide 80 for rotating the button 20 in response to the axial movement.

The cam guide 80 may be disposed on the button body 22 and the protrusion 50 may be disposed on the inner wall 40 at the distal end 42.

FIG. 6A is a representative view of the button 20 mounted within the rear frame 200 wherein the button 20 is in a "at rest" position and the cam guide 80 is represented as a right angle triangle. FIG. 6B is a representative view depicting a guided movement of the button 20 from the "at rest" position to a post-activation position showing a different position of the protrusion 50 in the post-activation position wherein a distal end 23 of the button 20 is below the inner wall 40 along the longitudinal axis 1000. The inner wall 40 and the button body 22 may comprise a cylindrical axis 2000 wherein the axis 2000 is coaxial with the longitudinal axis 1000 of the frame opening 201. Referring to FIGS. 6A and 6B, the cam guide 80 comprises a first end 81 and a second end 82 defining a radial distance D1 and an axial distance D2 of the cam guide 80 between the first and second ends 81, 82. The protrusion 50 is located at the first end 81 in the "at rest" position whereas a ramp 70 is located at the second end 82 of the cam guide 80 for abutting the protrusion 50 in the post activation position (see FIG. 6B).

In the "at rest position" as shown in FIG. 6A, the distal end 23 of the button body 22 is proximal to the protrusion 50. The protrusion 50 may comprise a rounded profile 501 for engaging the cam guide 80. When the button 20 is pressed, the button 20 moves axially into the housing 2 along an axial direction 1100 parallel to the longitudinal axis 1000. Engagement of the protrusion 50 with the cam guide 80 converts the axial movement of the button 20 into rotation of the button 20 until the protrusion 50 abuts the ramp 70 and is adjacent the second end 82 in the post activation position. An advantage of the ramp 70 is to limit movement of the button 20 upon rupturing of the rupturable substrate 33 thereby sending a tactile signal to the user that the button 20 has been activated and the user releases the button 20.

Figure 13A:
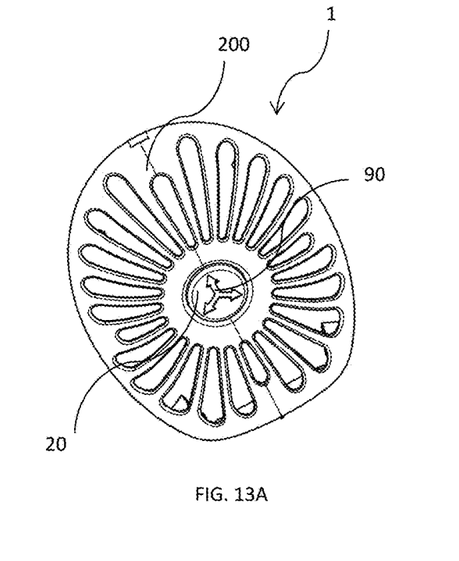
FIG. 13A is a rear perspective view of a volatile composition dispenser with a button in a first position before activation.
Figure 13B:
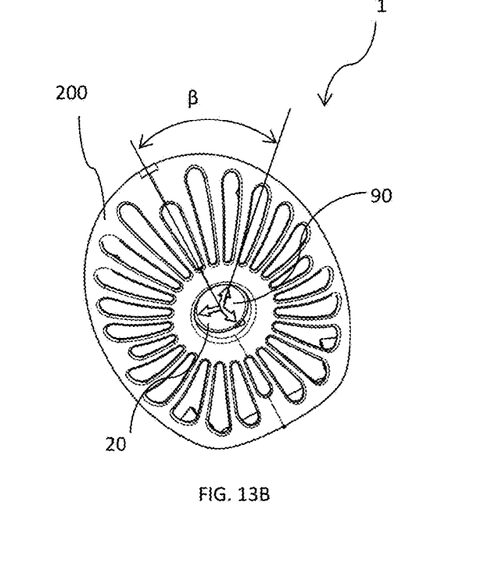
FIG. 13B is a rear perspective view of the button of FIG. 13A in a second position after activation.

A cam angle, $\alpha$ of the cam guide 80 may be configured to obtain a desired button stroke S (mm) and a rotation angle $\beta$ of the button 20 about the longitudinal axis 1000 and/or the cylindrical axis 2000 (shown in FIG. 13B). The desired button stroke may be a distance to be travelled by the button 20 along the longitudinal axis 1000 of the opening 201 in order to cause the rupture elements 37 of the rupture mechanism 34 to puncture the substrate 33.

By having the cam guide 80 and the protrusion 50 cooperating to move the button 20 axially along and rotate about the longitudinal axis 1000 in a clockwise or an anti-clockwise direction, the top 21 of the button 20 may have different orientations with respect to the rear frame 200 as shown in FIG. 13A and FIG. 13B.

A technical effect of the button 20 being movable axially and rotatable simultaneously is to increase a guiding area for guiding travel of the button 20 and to maintain the distal end 23 of the button body 22 parallel to a plane perpendicular to the longitudinal axis 1000 so as to engage the rupture mechanism 34 (in FIG. 3) for even rupturing of the rupturable substrate 33 (in FIG. 3), i.e. all the rupture elements 37 (in FIG. 3) pierce the rupturable substrate 33 upon activation.

A further advantage of the cam guide 80 is to enable distribution of pressure on the cartridge 30 (as shown in FIG. 3) which results from an activation force is applied by the user on the button 20. Accordingly, if the user exerts an excessive or sudden force, the movement of the button 20, any resultant pressure or energy may be absorbed through the engagement of the helical guide rail 80 and the protrusion 50 before the button 20 engages the rupture mechanism 34. Therefore, energy from the activation force may be transferred from the button 20 to the rupture mechanism 34 within the cartridge 30 in a controlled manner so as to enable efficient and controlled rupturing of the rupturable substrate 33 in the cartridge 30.

A ratio of the button stroke S to the button rotation angle $\beta$ may be 0.1 mm/degree. The cam angle $\alpha$ may be greater than the rotation angle $\beta$ of the button 20. A ratio of the cam angle $\alpha$ to the button rotation angle $\beta$ may be 1.3, and the button rotation angle may be in the range of 30° to 70°. Table 1 sets out different sets of corresponding values of the cam angle $\alpha$, the button rotation angle $\beta$ and the button stroke S for a small form factor volatile composition dispenser 1.

TABLE 1

| | Set | | | |
|---|---|---|---|---|
| | A | B | C | D |
| Button Stroke S | 4.25 mm | 3 mm | 4.5 mm | 5 mm |
| Button Rotation Angle $\beta$ | 42.5 degrees | 30 degrees | 45 degrees | 50 degrees |
| Cam Angle $\alpha$ | 55.25 degrees | 39 degrees | 58.5 degrees | 65 degrees |

The cam guide 80 may be a helical guide rail on the inner wall 40 or the button body 22 and the cam angle $\alpha$ of the helical guide rail 80 relative to the cylindrical axis 2000 of the inner wall 40 or the button body 22 may be defined as:

$$\alpha = \arctan(D1/D2), \text{ wherein:}$$

D1=radial distance of the helical guide rail between the first and second ends;
D2=axial distance of the helical guide rail between the first and second ends The helical guide rail 80 may be a continuous track extending circumferentially around the inner wall 40 or the button body 22. The radial distance of the guide rail 80, D1 may be defined as, $$D1 = 2\pi r$$

wherein r=radius of the inner wall 40 or the button body 22 (mm)

Alternatively, the helical guide rail 80 may be discontinuous, and is a plurality of parallel helical tracks 80 extending circumferentially around the button body 22. The helical tracks 80 are configured to be of equivalent shape and size and therefore, the radial distance of the guide rail, $D1^1$ may be defined as, $$D1^1 = 2\pi r/(\text{number of helical tracks})$$

wherein r=radius of the button body (mm)

An advantage of the helical guide rail 80 being discontinuous compared to a continuous guide rail is to provide a shorter button stroke and a more compact design of the button 20 and consequently a more compact dispenser design.

Figure 7A:
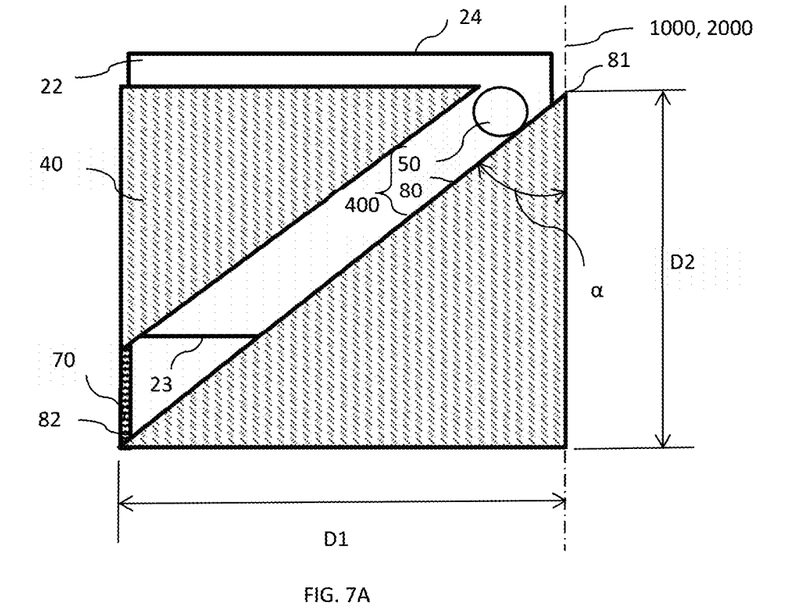
FIGS. 7A and 7B are schematic drawings which depict the movement of an alternative embodiment of a button within a rear frame for a volatile composition dispenser.
Figure 7B:
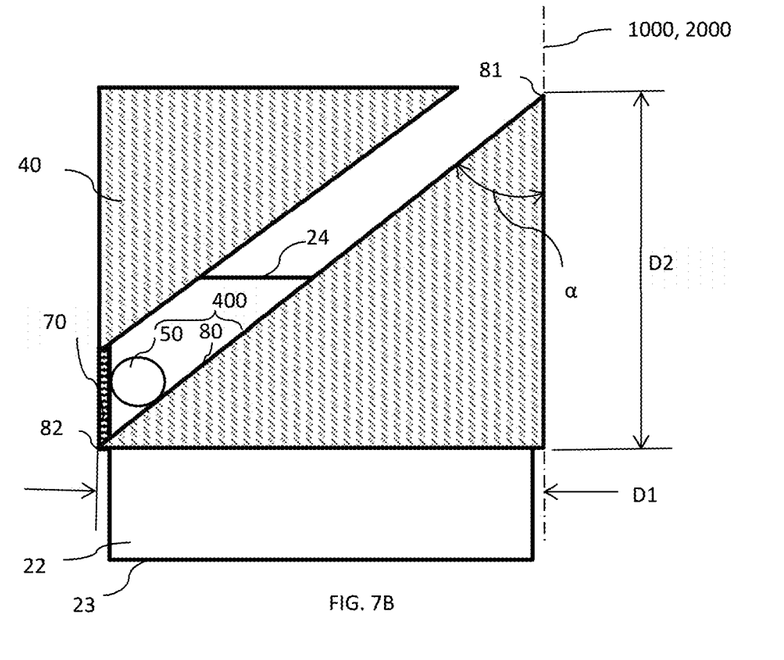
Figure 8:
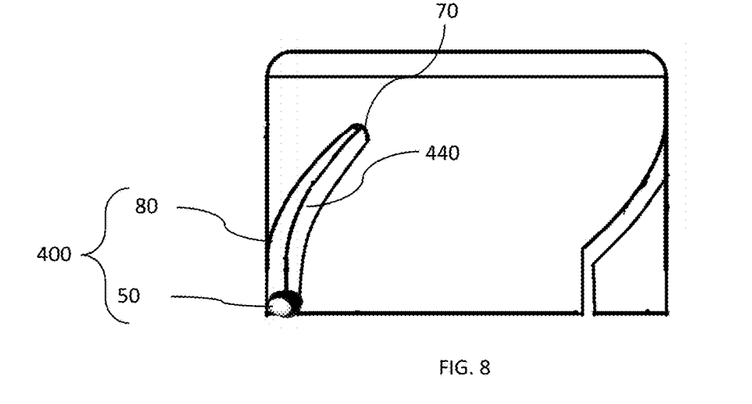
FIGS. 8 and 9 are partial perspective views showing different geometry configurations of a helical guide rail and protrusions for the dispenser.
Figure 9:
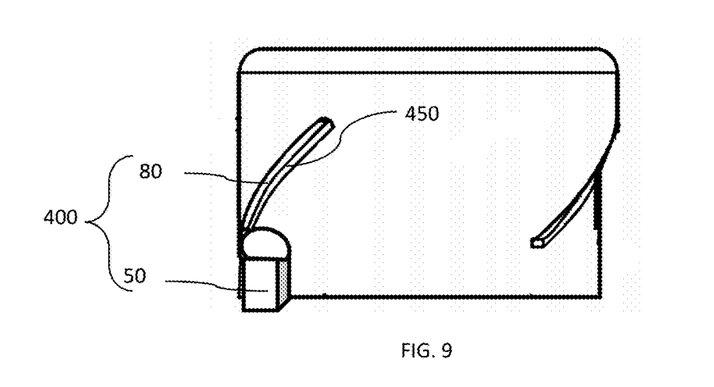

Referring to FIGS. 7A and 7B, the helical guide rail 80 may be disposed on the inner wall 40 and the protrusion 50 may be disposed on the button body 22 proximally to a proximal end 24 of the button body 22. Specifically, the helical guide rail 80 is disposed centrally on the button body 22 and the protrusion 50 is located at a distal end of the inner wall 40. FIGS. 8 and 9 show different configurations of the helical guide rail 80 and the protrusion 50. Referring to FIG. 8, the helical guide rail 80 may comprise one or more helical grooves 440 formed in the button body 22. A protrusion 50 may be a roller or a pin attached to the inner wall 40. An advantage of forming helical grooves 440 is that less material may be used to manufacture the button 20, thus saving product material costs. Further, an end 441 of the helical groove 440 performs the same function as the ramp 70 to limit movement of the button 20 after activation. Alternatively, as shown in FIG. 9, the helical guide rail 80 may comprise one or more helical ribs 450 extending radially from the button body 22.

Figure 10:
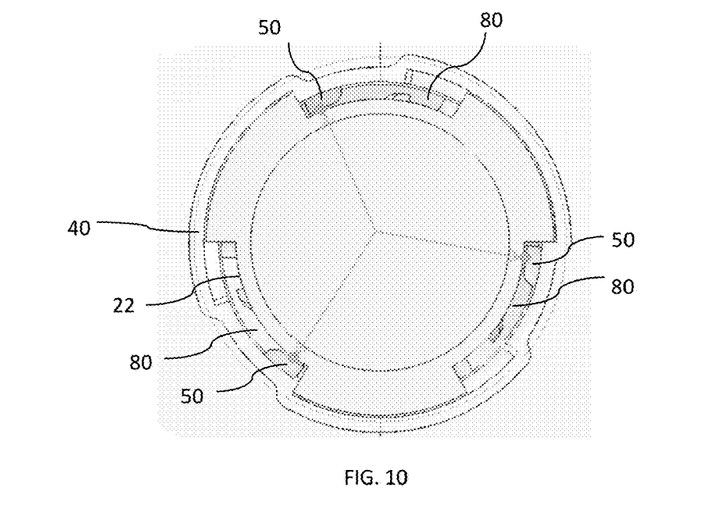
FIG. 10 is an interior view of a configuration of protrusions between a button and a rear frame according to an embodiment in a first position before activation.

FIG. 10 is a rear view of the button 20 within the rear frame 200 before activation, i.e. in a "at rest" position. Further, as shown for example in FIG. 14, one or more protrusions 50 are spaced and located at the distal end 42 of the inner wall 40 and arranged to engage each of the guide rails 80 defining three points of contact (not shown) (also known as a three-point contact) between the button body 22 and the inner wall 40. The three-point contact defines a stable support plane for the button 20 when pressed for example, in an unintended location such as an off-center location on the top 21 (shown in FIG. 11) and minimizes tilting of the button 20 during movement of the button 20 with respect to the inner wall 40.

Figure 11:
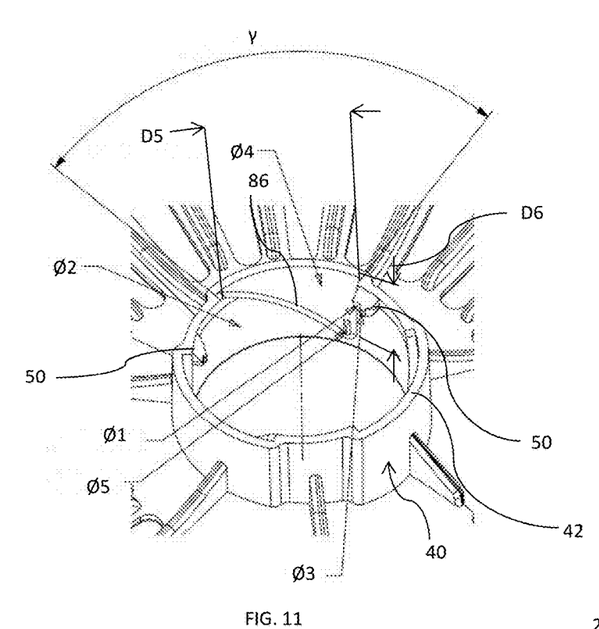
FIG. 11 is a partial perspective view of a rear frame for a volatile composition dispenser.
Figure 12A:
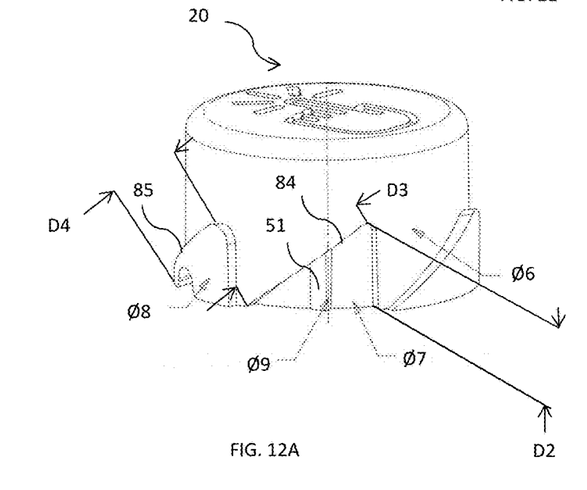
FIG. 12A is a perspective view of a button the rear frame of FIG. 11.
Figure 12B:
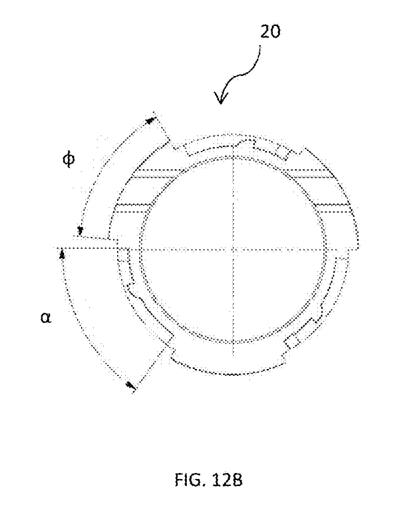
FIG. 12B is a bottom view of the button of FIG. 12A.

FIG. 11 is a perspective view of the rear frame 200 of FIG. 3 (partially shown), FIG. 12A is a perspective view of he button 20 and FIG. 12B is a bottom view of the button 20. One or more protrusions 50 are disposed at the distal end 42 of the inner wall 40 wherein the protrusion 50 is aligned for engaging the cam guide 80 of the button body 22. The cam guide 80 may comprise a plurality of first cam tracks 84 formed on the button body 22. The first cam tracks 84 are radially spaced apart on the button body 22 for engaging the protrusions 50 on the distal end 42 of the inner wall 40. The cam guide 80 may further comprise a plurality of second cam tracks 85 intermediate the first cam tracks 84.

Specifically, the second cam tracks 85 extend radially outward from and spaced circumferentially on the button body 22 and arranged to engage mating cam track 86 formed on the inner wall 40 upon insertion of the button 20 in the inner wall 40. Each second cam track 85 and a mating cam track 86 may be configured to correspond in shape or profile to the first step 84 so as to define a continuous cam profile for rotation of the button 20 about the longitudinal axis 1000 and axial movement of the button 20 along the longitudinal axis 1000.

Further, as shown in FIG. 12A, indicia 90 may be made on the button 20. For example as shown in FIG. 13A, the indicia 90 may be configured to indicate various orientations of the top 21 of the button 20 upon axial movement and rotation of the button 20 relative to the rear frame 200. For example, the top 21 of the button 20 may be in one orientation relative to the rear frame 200 in the "at rest" position (FIG. 13A) and in an alternate orientation relative to the rear frame 200 in the post-activation position (FIG. 13B).

Figure 14A:
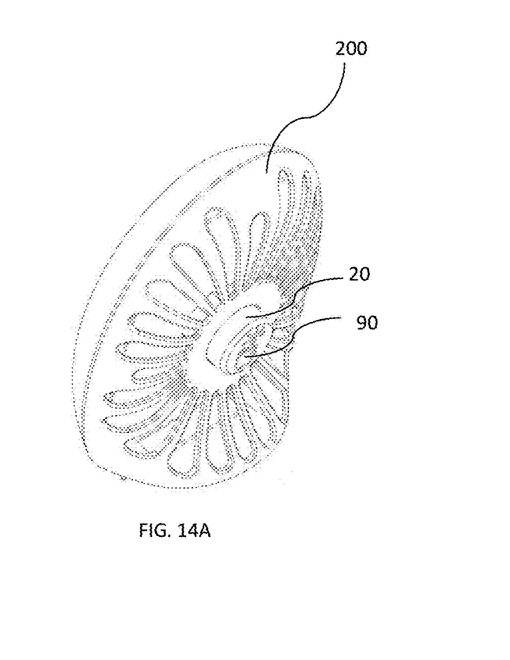
FIG. 14A is a rear perspective view of a volatile composition dispenser with a button positioned above a periphery of an opening in a rear frame in a first position before activation.
Figure 14B:
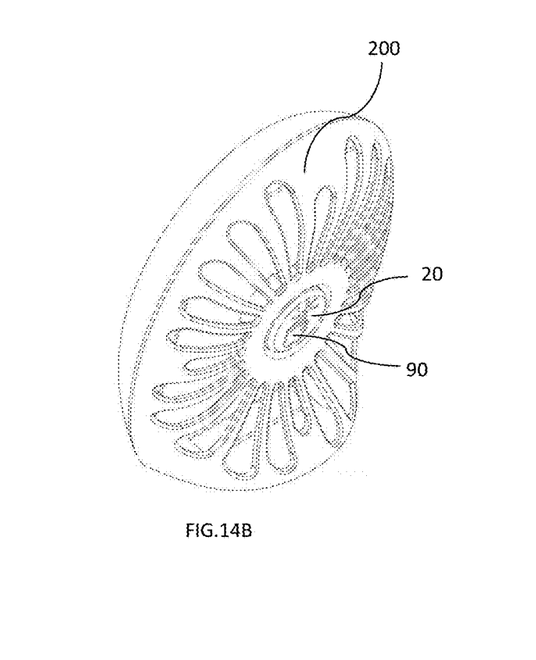
FIG. 14B is a rear perspective view of the button of FIG. 14A in a second position after activation.

Further, the second cam tracks 85 and the mating cam tracks 86 may be configured to allow the button 20 to be arranged within the frame 200 at a height relative to the distal end 42 of the inner wall 40. The height may be varied so that upon assembly, the button 20 may be either flush with the periphery 207 of the opening 201 in the first position (as shown in FIG. 13A) or extending above the periphery 207 of the opening 201 in the first position (as shown in FIG. 14A). A second protrusion 51 may be disposed on the first cam track 84 for engaging with and moving past the protrusion 50 such that the button 20 may be interlocked with the rear frame 200 after activation.

The inner wall 40, the protrusion 50 and the frame 200 may be molded and form a unitary unit and may comprise plastic for ease of manufacturing. Similarly, the helical guide rail 80 and the button 20 may also be molded and form a unitary plastic component. Alternatively, the button 20, and the frame 200 and the protrusion 50 may comprise sheet metal, such as spring steel, and may be stamped or milled to form a unitary metal component.

The volatile composition dispenser 1 may comprise a small form factor such as a form factor similar to a computer mouse so as for ergonomic fit in the hand of the user and ease of use. Physical specifications of the inner wall 40, the button 20, the protrusion 50, and the guide rail 80 may be configured based on a specified button stroke S (millimeters) and/or a specified rotation angle β (degrees) of the button 20 relative to the longitudinal axis 1000 as shown in FIG. 13B. Referring to FIGS. 11, 12A and 12B, Table 2 sets out physical specifications of the inner wall 40, the button 20, the protrusion 50 and the guide rail 80 based on a button stroke S of 4.25 mm and a rotation angle β of 42.5 degrees. A correlation between a button stroke S and a rotation angle β, S/β may be 0.1 mm/degree. Therefore, it will be appreciated by a person skilled in the arts that the present invention is not limited to the physical specifications of Table 2. Specifically, the physical specifications may be modified based on a desired button stroke or button rotation angle using the correlation of S/β=0.1 mm/degree. Further, the physical specifications may be modified by using a ratio of the cam angle, α to the button rotation angle, β being 1.3.

TABLE 2

| Symbol as shown in FIGS. 11, 12A, 12B | Button Stroke S = 4.25 mm<br>Button Rotation Angle, β = 42.5 degrees |
|---|---|
| D1 (mm) | — |
| D2 (mm) | 4.63 |
| D3 (mm) | 8.9 |
| D4 (mm) | 9.95 |
| D5 (mm) | 13.85 |
| D6 (mm) | 6.6 |
| Diameter Ø1 (mm) | 14.75 |
| Diameter Ø2 (mm) | 16.27 |
| Diameter Ø3 (mm) | 14.36 |
| Diameter Ø4 (mm) | 17.76 |
| Diameter Ø5 (mm) | 17.15 |
| Diameter Ø6 (mm) | 16.03 |
| Diameter Ø7 (mm) | 14.41 |
| Diameter Ø8 (mm) | 17.34 |
| Diameter Ø9 (mm) | 15.53 |
| Angle α (degrees) | 55.25 |
| Angle γ (degrees) | 77.07 |
| Angle φ (degrees) | 55.17 |

The internal components of the cartridge 30 as shown in FIG. 3 may be characterized as follows. For example, dimensions of the container 32 may be configured to hold about 1 ml to about 50 ml of a liquid volatile composition. Alternatively, the reservoir 52 may hold about 2 ml to about 30 ml, alternatively about 2 ml to about 10 ml, alternatively about 2 ml to about 8 ml, alternatively about 4 ml to about 6 ml, alternatively about 2 ml, alternatively about 6 ml of a liquid volatile composition. Further, a shape of the container 32 may be configured to correspond to a shape of the opening 101 of the front cover 100. For example, the container 32 may define a substantially elliptical or oval shape and its width to length ratio may be about 1:2 to 1:2.5.

The rupturable substrate 33 can be made of any material that ruptures with applied force, with or without the presence of an element to aid in such rupture. Because the rupturable substrate 33 is intended to contain a volatile material while in storage, it may be made from any barrier material that prevents evaporation of the volatile material prior to its intended use. Such materials may be impermeable to vapors and liquids. Suitable barrier materials for the rupturable substrate 33 include a flexible film, such as a polymeric film, a flexible foil, or a composite material such as foil/polymeric film laminate. Suitable flexible foils include a metal foil such as a foil comprised of a nitrocellulose protective lacquer, a 20 micron aluminum foil, a polyurethane primer, and 15 g/m2 polyethylene coating (Lidfoil 118-0092), available from Alcan Packaging. Suitable polymeric films include polyethylene terephtalate (PET) films, acrylonitrile copolymer barrier films such as those sold under the tradename Barex® by INOES, ethylene vinyl alcohol, and combinations thereof. It is also contemplated that coated barrier films may be utilized as a rupturable substrate 33. Such coated barrier films include metallized PET, metalized polypropylene, silica or alumina coated film may be used. Any barrier material, whether coated or uncoated, may be used alone and or in combination with other barrier materials.

configured to condition, modify, or otherwise change the atmosphere and may include compositions suitable for the purposes of providing fragrances, air fresheners, deodorizers, odor eliminators, malodor counteractants, insecticides, insect repellants, medicinal substances, disinfectants, sanitizers, mood enhancers, and aromatherapy aids. A list of the suitable volatile materials is shown in Table 2 below.

TABLE 3

| Purpose | Volatile Material |
| --- | --- |
| Providing fragrances | Perfume oil, volatile essential oils, volatile organic compound, synthetically or naturally formed materials. Examples include, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and the like. Suitable crystalline solids include but are not limited to vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like. |
| Neutralize malodors | Suitable malodor compositions include reactive aldehydes and ionones |

The rupture element 37 can be injection, compression, or pressure molded using a polyolefin, such as polyethylene or polypropylene; polyester; or other plastics known to be suitable for molding. The rupture element 130 could also be made by thermoforming with a discrete cutting step to remove parts not wanted.

The membrane 39 may have an average pore size of about 0.01 to about 0.06 microns, alternatively from about 0.01 to about 0.05 microns, alternatively about 0.01 to about 0.04 microns, alternatively about 0.01 to about 0.03 microns, alternatively about 0.02 to about 0.04 microns, alternatively about 0.02 microns. Further, the membrane 39 may be filled with any suitable filler and plasticizer known in the art. Fillers may include finely divided silica, clays, zeolites, carbonates, charcoals, and mixtures thereof. The microporous membrane 39 may be filled with about 50% to about 80%, by total weight, of silica, alternatively about 60% to about 80%, alternatively about 70% to about 80%, alternatively about 70% to about 75%. A thickness of the membrane 39 may be about 0.01 mm to about 1 mm, alternatively between about 0.1 mm to about 0.4 mm, alternatively about 0.15 mm to about 0.35 mm, alternatively about 0.25 mm.

Still further, an evaporative surface area of the microporous membrane 39 may be about 2 cm$^2$ to about 100 cm$^2$, alternatively about 2 cm$^2$ to about 25 cm$^2$, alternatively about 10 cm$^2$ to about 50 cm$^2$, alternatively about 10 cm$^2$ to about 45 cm$^2$, alternatively about 10 cm$^2$ to about 35 cm$^2$, alternatively about 15 cm$^2$ to about 40 cm$^2$, alternatively about 15 cm$^2$ to about 35 cm$^2$, alternatively about 20 cm$^2$ to about 35 cm$^2$, alternatively about 30 cm$^2$ to about 35 cm$^2$, alternatively about 35 cm$^2$. Accordingly, the rear frame 200 may be sized and shaped to fit the evaporative surface area of the membrane 39.

Suitable microporous membranes for the present invention include a microporous, ultra-high molecular weight polyethylene (UHMWPE) optionally filled with silica as described in U.S. Pat. No. 7,498,369. Such UHMWPE microporous membranes include Daramic™ V5, available from Daramic, Solupor®, available from DSM (Netherlands), and Teslin™, available from PPG Industries, and combinations thereof.

A volatile material or composition suitable for use in the cartridge 30 for a volatile composition dispenser 1 may be An example is shown below:

A. A volatile composition dispenser comprising:
a housing (10) comprising a rear frame having a frame opening (201) and a longitudinal axis (1000) extending centrally within said opening (201);
a rupturable cartridge (30) placed within said housing (10);
an inner wall (40) extending from the frame opening (201), wherein the inner wall (40) has a proximal end (41) at a periphery (207) of the opening (201) and a distal end (42);
a push button (20) movably disposed within the frame opening (201) for rupturing the cartridge (30), wherein the push button (20) includes a button body (22) and is axially movable along and rotatable about the longitudinal axis (1000) at a rotation angle, β (degrees);
a cam guide (80) disposed on the inner wall (40) or the button body (22), wherein the cam guide comprises a cam angle, α (degrees) relative to a cylindrical axis (2000) of the inner wall (40) or the button body (22), wherein α>β; and
a protrusion (50) disposed on the other of the inner wall (40) or the button body (22) wherein the protrusion (50) is engaged with the cam guide (80) in response to the axial movement of the button (20) when pushed.

B. A volatile composition dispenser (1) according to paragraph A, wherein the protrusion (50) comprises a curved profile for engaging the cam guide (80).

C. A volatile composition dispenser (1) according to paragraph A, wherein the inner wall (40) and the button body (22) are substantially cylindrical, the cam guide (80) comprising a first end (81) and a second end (81), wherein a ramp (70) is located at one of the first and second ends (81, 82) of the cam guide (80); wherein the protrusion (50) is spaced from the ramp (70) in a first position and abuts the ramp (70) in a second position to limit movement of the button (20) when pushed.

D. A volatile composition dispenser (1) according to paragraph C, wherein the cam guide is a helical guide rail wherein the cam angle, α is defined as α=arctan(D1/D2), wherein D1=radial distance of the helical guide rail between the first and second ends;

D2=axial distance of the helical guide rail between the first and second ends; and wherein α is in the range of 15° to 45°.

D. A volatile composition dispenser (1) according to paragraph C, wherein the helical guide rail (80) is continuous, wherein D1=2πr, wherein r=radius of the inner wall or the button body.

E. A volatile composition dispenser (1) according to paragraph C, wherein the helical guide rail (80) is discontinuous and comprises a plurality of helical tracks of substantially equivalent shape and size, wherein D1=2πr/(number of helical tracks), wherein r=radius of the inner wall or the button body.

F. A volatile composition dispenser (1) according to paragraph A, wherein a ratio of the cam angle, α to the button rotation angle, β is 1.3.

G. A volatile composition dispenser (1) according to paragraph F, wherein the cam guide (80) is discontinuous and comprises a plurality of first cam tracks (84) on the inner wall or the button body, wherein the plurality of first cam tracks (84) are radially spaced apart on the inner wall or the button body and engage protrusions (50) on the other of the inner wall or button body.

H. A volatile composition dispenser (1) according to paragraph G, wherein the cam guide (80) comprises second cam tracks (85) intermediate the first cam tracks (84), wherein the second cam tracks (85) engages mating cam tracks (86) on the other of the inner wall or button body.

I. A volatile composition dispenser (1) according to paragraph A, wherein the cam guide (80) comprises one or more cam grooves formed in the inner wall or the button body.

J. A volatile composition dispenser (1) according to paragraph A, wherein the cam guide (80) comprises one or more cam ribs extending radially from the inner wall or the button body.

K. A volatile composition dispenser (1) according to paragraph A, wherein the cam guide (80) and the button (20) form a unitary unit.

L. A volatile composition dispenser (1) according to paragraph A, wherein the protrusion (50), the inner wall (40) and the rear frame (200) form a unitary unit.

M. The volatile composition dispenser (1) according to paragraph A, further comprising indicia disposed on a top of the push button.

O. A volatile composition dispenser (1) according to paragraph A, wherein three protrusions (50) are radially spaced apart and located at the distal end (42) of the inner wall (40) for engaging the cam guide (80) to define three points (83) of contact between the button body (22) and the inner wall (40).

J. A method of activating a volatile composition dispenser, the method comprising: providing a volatile composition dispenser comprising:

a housing (10) comprising a rear frame (200) having a frame opening (201) and a longitudinal axis (1000) disposed centrally within said opening (201) and a rupturable cartridge (30) placed within said housing (10);

an inner wall (40) extending from the frame opening (201), wherein the inner wall (40) has a proximal end (41) at a periphery (207) of the opening (201) and a distal end (42);

moving a push button (20) axially movable along the longitudinal axis (1000); and guiding movement of the push button (20) through engaging a protrusion (50) disposed on the other of the inner wall (40) or the button body (22) with a cam guide (80) disposed on the inner wall (40) or the button body (22).

K. The method of activating according to paragraph J, further comprising:

rotating the push button at a rotation angle, β (degrees) in response to the axial movement of the push button (20) wherein the cam guide comprises a cam angle, α (degrees) relative to a cylindrical axis (2000) of the inner wall (40) or the button body (22), wherein α>β.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A volatile composition dispenser comprising:

a housing comprising a rear frame having a frame opening and a longitudinal axis extending centrally within said opening;

a rupturable cartridge placed within said housing;

an inner wall extending from the frame opening, wherein the inner wall has a proximal end at a periphery of the opening and a distal end;

a push button movably disposed within the frame opening for rupturing the cartridge, wherein the push button includes a button body and is axially movable along and rotatable about the longitudinal axis at a rotation angle, β(degrees);

a cam guide disposed on the inner wall or the button body, wherein the cam guide comprises a cam angle, α(degrees) relative to a cylindrical axis of the inner wall or the button body, wherein α>β; and a protrusion disposed on the other of the inner wall or the button body wherein the protrusion is engaged with the cam guide for simultaneously rotating the button in response to the axial movement of the button when pushed along the longitudinal axis.

2. A volatile composition dispenser according to claim 1, wherein the protrusion comprises a curved profile for engaging the cam guide.

3. A volatile composition dispenser according to claim 1, wherein the inner wall and the button body are substantially cylindrical, the cam guide comprising a first end and a second end, wherein a ramp is located at one of the first and second ends of the cam guide; wherein the protrusion is spaced from the ramp in a first position and abuts the ramp in a second position to limit movement of the button when pushed.

4. A volatile composition dispenser according to claim 3, wherein the cam guide is a helical guide rail wherein the cam angle, α is defined as $\alpha = \arctan(D1/D2)$, wherein D1 = radial distance of the helical guide rail between the first and second ends;

D2 = axial distance of the helical guide rail between the first and second ends; and wherein α is in the range of 15° to 45°.

5. A volatile composition dispenser according to claim 4, wherein the helical guide rail is continuous, wherein D1=2πr, wherein r=radius of the inner wall or the button body.

6. A volatile composition dispenser according to claim 4, wherein the helical guide rail is discontinuous and comprises a plurality of helical tracks of substantially equivalent shape and size, wherein D1=2πr/(number of helical tracks), wherein r=radius of the inner wall or the button body.

7. A volatile composition dispenser according to claim 1, wherein a ratio of the cam angle, α to the button rotation angle, β is 1.3.

8. A volatile composition dispenser according to claim 7 further comprising a plurality of the protrusions, wherein the cam guide is discontinuous and comprises a plurality of first cam tracks on the inner wall or the button body, wherein the plurality of first cam tracks are radially spaced apart on the inner wall or the button body and engage the plurality of protrusions on the other of the inner wall or button body.

9. A volatile composition dispenser according to claim 8, wherein the cam guide comprises second cam tracks intermediate the first cam tracks, wherein the second cam tracks engage mating cam tracks on the other of the inner wall or button body.

10. A volatile composition dispenser according to claim 1, wherein the cam guide comprises one or more cam grooves formed in the inner wall or the button body.

11. A volatile composition dispenser according to claim 1, wherein the cam guide comprises one or more cam ribs extending radially from the inner wall or the button body.

12. A volatile composition dispenser according to claim 1, wherein the cam guide and the button form a unitary unit.

13. A volatile composition dispenser according to claim 1, wherein the protrusion, the inner wall and the rear frame form a unitary unit.

14. The volatile composition dispenser according to claim 1, further comprising indicia disposed on a top of the push button.

15. A volatile composition dispenser according to claim 1, wherein three protrusions are radially spaced apart and located at the distal end of the inner wall for engaging the cam guide to define three points of contact between the button body and the inner wall.

* * * * *